(12) United States Patent
Sullivan et al.

(10) Patent No.: US 6,533,806 B1
(45) Date of Patent: Mar. 18, 2003

(54) BALLOON YIELDED DELIVERY SYSTEM AND ENDOVASCULAR GRAFT DESIGN FOR EASY DEPLOYMENT

(75) Inventors: Jason Sullivan, Wayne, NJ (US); Ellen Golds, Hasting-on-Hudson, NY (US); David Tseng, Cambridge, MA (US); Jeff Boatman, Lincoln Park, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/409,620

(22) Filed: Oct. 1, 1999

(51) Int. Cl.⁷ .................................................. A61F 2/06
(52) U.S. Cl. ...................................................... 623/1.11
(58) Field of Search ............................... 623/1.11, 1.13, 623/1.12, 1.2, 1.23, 1.36, 1.38

(56) References Cited

U.S. PATENT DOCUMENTS

| | | |
|---|---|---|
| 5,078,720 A | 1/1992 | Burton et al. |
| 5,190,058 A | 3/1993 | Jones et al. |
| 5,199,951 A | 4/1993 | Spears |
| 5,234,425 A | 8/1993 | Fogarty et al. |
| 5,316,023 A | 5/1994 | Palmaz et al. |
| 5,366,472 A | 11/1994 | Hillstead |
| 5,372,600 A | 12/1994 | Beyar et al. |
| 5,403,341 A * | 4/1995 | Solar ........................... 606/198 |
| 5,409,495 A | 4/1995 | Osborn |
| 5,453,090 A | 9/1995 | Martinez et al. |
| 5,534,007 A | 7/1996 | St. Germain et al. |
| 5,571,135 A | 11/1996 | Fraser et al. |
| 5,571,171 A | 11/1996 | Barone et al. |
| 5,626,602 A | 5/1997 | Gianotti et al. |
| 5,630,830 A | 5/1997 | Verbeek |
| 5,639,276 A | 6/1997 | Weinstock et al. |
| 5,647,857 A | 7/1997 | Anderson et al. |
| 5,662,700 A | 9/1997 | Lazarus |
| 5,665,114 A * | 9/1997 | Weadock et al. .......... 623/1.34 |
| 5,669,932 A | 9/1997 | Fischell et al. |
| 5,674,241 A * | 10/1997 | Bley et al. .................. 606/198 |
| 5,690,643 A | 11/1997 | Wijay |
| 5,693,083 A | 12/1997 | Baker et al. |
| 5,700,286 A * | 12/1997 | Tartaglia et al. ............. 604/104 |
| 5,713,917 A * | 2/1998 | Leonhardt et al. .......... 606/194 |
| 5,749,922 A | 5/1998 | Slepian et al. |
| 5,755,780 A | 5/1998 | Finch, Jr. et al. |
| 5,792,144 A | 8/1998 | Fischell et al. |
| 5,797,949 A | 8/1998 | Parodi |
| 5,807,398 A | 9/1998 | Shaknovich |
| 5,824,046 A * | 10/1998 | Smith et al. ................ 623/1.15 |

(List continued on next page.)

FOREIGN PATENT DOCUMENTS

| | | |
|---|---|---|
| EP | 0815805 A2 | 6/1997 |
| EP | 0839506 A1 | 10/1997 |
| WO | WO98/25544 | 6/1998 |
| WO | WO99/32051 | 7/1999 |

OTHER PUBLICATIONS

U.S. patent application Ser. No. 09/668,496, Yang, filed Sep. 22, 2000.
U.S. patent application Ser. No. 09/750,934, Yang et al., filed Dec. 29, 2000.
U.S. patent application Ser. No. 09/829,295, Yang, filed Apr. 9, 2001.

*Primary Examiner*—Michael J. Milano
*Assistant Examiner*—(Jackie) Tan-Uyen T. Ho
(74) *Attorney, Agent, or Firm*—Vidas, Arrett & Steinkraus

(57) ABSTRACT

An endoluminal prosthetic delivery system provides a delivery sheath possessing a yield strength capable of allowing implantation of the prosthesis with increased efficiency. An endoluminal prosthesis is inserted in a body in a radially compressed condition, and expanded at an implantation site, whereby a delivery sheath or the prosthesis itself possesses a yield strength sufficient to allow radial expansion of the prosthesis. A method of implanting an endoluminal prosthesis is also herein provided.

14 Claims, 7 Drawing Sheets

U.S. PATENT DOCUMENTS

| | | |
|---|---|---|
| 5,843,158 A | 12/1998 | Lenker et al. |
| 5,980,530 A * | 11/1999 | Willard et al. ............... 606/195 |
| 6,015,432 A * | 1/2000 | Rakos et al. ................ 623/1.13 |
| 6,063,112 A | 5/2000 | Sgro |
| 6,179,878 B1 * | 1/2001 | Duerig et al. ................ 128/898 |
| 6,331,186 B1 * | 12/2001 | Wang et al. ................ 623/1.11 |
| 6,350,277 B1 | 2/2002 | Kocur ........................ 623/1.11 |
| 6,432,130 B1 | 8/2002 | Hanson ...................... 623/1.11 |

* cited by examiner

BALLOON YIELDED DELIVERY SYSTEM AND ENDOVASCULAR GRAFT DESIGN FOR EASY DEPLOYMENT

FIELD OF THE INVENTION

The present invention relates generally to a system and method of delivering an endoluminal prosthesis within a body lumen. More particularly the present invention provides a delivery device retaining an endoluminal prosthesis during delivery and additionally for the deployment of the endoluminal prosthesis at a target site within the lumen.

BACKGROUND OF THE INVENTION

Endoluminal prostheses are typically used to repair, replace, or otherwise correct a diseased or damaged blood vessel. An artery or vein may be diseased in a variety of ways. The prosthesis may therefore be used to prevent or treat a wide variety of defects such as stenosis of the vessel, thrombosis, occlusion, or an aneurysm.

One type of endoluminal prosthesis used in treatment and repair of diseases in various blood vessels is a stent. A stent is a generally longitudinal tubular device which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of materials, including textile and non-textile materials. Grafts also generally have an unexpanded insertion diameter and an expanded implantation diameter which is greater than the unexpanded diameter.

It is also known to combine a stent and a graft to form a composite endoluminal prosthesis. Such a composite medical device provides additional support for blood flow through weakened sections of a blood vessel. In endovascular applications the use of a stent/graft combination is becoming increasingly important because the combination not only effectively allows the passage of blood therethrough, but also ensures the implant will remain open.

It is also known to provide delivery systems for delivering such prostheses intraluminally. These delivery systems generally include catheters with the prosthesis removably mounted to the distal end of the catheter. Quite often a catheter, introducer sheath, or other similar retaining means, is disposed over the prosthesis to removably support the prosthesis on the catheter. Once the prosthesis is situated in the target site in the lumen, the catheter is removed from the prosthesis.

In order to activate the prosthesis to its expanded implantation diameter, however, it is usually required to pull the sheath or retaining means away from the prosthesis to allow the expansion. The catheter typically retains and delivers the prostheses in a radially contracted state in its unexpanded insertion diameter, and removal of the catheter sheath allows expansion to the expanded implantation diameter.

Delivery and removal of the catheter sheath, however, to implant and/or activate the prosthesis presents several problems. First, catheter movement can disturb or move the introducer sheath at the wound site where the catheter is inserted into the vessel, thereby resulting in premature deployment of the prosthesis. Secondly, in tortuous anatomy, the added friction caused by rubbing the outer catheter against the vessel can make delivery and deployment of the prosthesis difficult. The translation of control movements from the proximal to the distal end of the catheter is imprecise, jerky and in some instances impossible due to the increased friction caused by tortuosity. Thirdly, delivery of the sheathed prosthesis can create trauma to the endothelium over the entire length of the catheter.

It is therefore desirous to provide an endoluminal prosthetic delivery system which delivers and activates an endoluminal prosthesis to its expanded implantation diameter without requiring removal of the catheter sheath in order to expand the prosthesis.

SUMMARY OF THE INVENTION

It is an advantage of the present invention to provide a catheter delivery system which delivers an endoluminal prosthesis to a target site without requiring the removal of an outer sheath or retaining structure.

It is also an advantage of the present invention to provide a delivery system for an endoluminal prosthesis which provides for delivery and expansion while still contained within the catheter sheath.

It is also an advantage of the present invention to provide an endoluminal prosthesis delivery system of reduced profile for effective delivery of a prosthesis through narrow body vessels.

It is a further advantage of the present invention to provide an endoluminal prosthesis delivery system which can remain implanted in a body vessel with the prosthesis.

In efficient attainment of these advantages, the present invention provides an endoluminal prosthesis delivery system comprising a tubular endoluminal prosthesis having a luminal surface and an opposed exterior surface, said prosthesis being radially expandable from a compressed condition under a first radially expansive force and a second radially expansive force greater than said first expansive force; and a delivery sheath maintaining said prosthesis in said compressed condition, said delivery sheath possessing a yield strength greater than said first expansive force of said prosthesis, and less than said second expansive force.

The present invention also provides a method of implanting an endoluminal prosthesis comprising loading a tubular endoluminal prosthesis in a reduced diameter in a compressed condition within a delivery sheath, said prosthesis being radially expandable under a first radially expansive force and a second radially expansive force greater than said first radially expansive force, said delivery sheath having a yield strength sufficient to retain said prosthesis in reduced diameter; intraluminally delivering said prosthesis to an implantation site wherein said second radially expansive force of said prosthesis is activated, said second radially expansive force being sufficient to surpass said yield strength of said delivery sheath.

In another method of implanting the prosthesis, a radially expansive force may be applied to the prosthesis by a balloon catheter, said radially expansive force being sufficient to surpass said yield strength of said delivery sheath.

DETAILED DESCRIPTION OF THE INVENTION

The following is a detailed description of the preferred embodiments of the present invention. The description is meant to describe preferred embodiments, and is not meant to limit the invention in any way.

The present invention provides a system for delivery of an expandable prosthesis to a target site. The delivery system may include a catheter having an expandable balloon. The endoluminal prosthesis is supported over the balloon by a catheter sheath. The present invention provides a catheter sheath which has a yield strength greater than a first expansive force exhibited by the endoluminal prosthesis, but less than a second expansive force of either the balloon or of the prosthesis so as to retain the prosthesis in a collapsed condition during delivery and to provide for deployment of the expandable prosthesis upon application of the expansive force from the balloon without removal of the sheath.

Various prostheses may be employed in the present invention. A stent, vascular graft, stent covered with a graft, or other stent/graft combinations may be employed. The prosthesis may be self-expanding, or expandable by other expansion mechanisms, such as balloon expansion. In the case where the prosthesis is self-expanding, the second radially expansive force may be a result of the self-expansion of the prosthesis, and a balloon catheter will not be necessary. The term radially expansive force as used in this disclosure, refers to the force which may be applied to the tubular prosthesis and/or delivery sheath to provide for circumferential expansion. It could be equal to zero.

Among the various stents which may be employed include, without limitation, self-expanding stents and balloon expandable stents. The configuration of the stent may also be chosen from a host of geometries. The stents may be capable of radially expanding, as well as contracting, and in this sense can best be described as radially distensible or deformable. Self-expanding stents include those that have a spring-like action which causes the stent to radially expand, or stents which expand due to memory properties of the stent material for a particular configuration at a certain temperature. Nitinol is one material which has the ability to perform well while both in spring-like mode, as well as in a memory mode based on temperature. Other materials (as well as combinations of materials, or alloys, or both) are of course contemplated, such as stainless steel, platinum, gold, titanium, and other biocompatible metals, as well as polymeric stents.

Endovascular grafts may also be used in the present invention. As mentioned above, endovascular grafts may be used alone or in conjunction with a stent. Many combinations are possible. For example, a stent may have an outer tubular cover, inner tubular cover, or both. Many other variations of the stent/graft combination, as well as other types of prostheses may also be used with the present invention.

Figure 1:
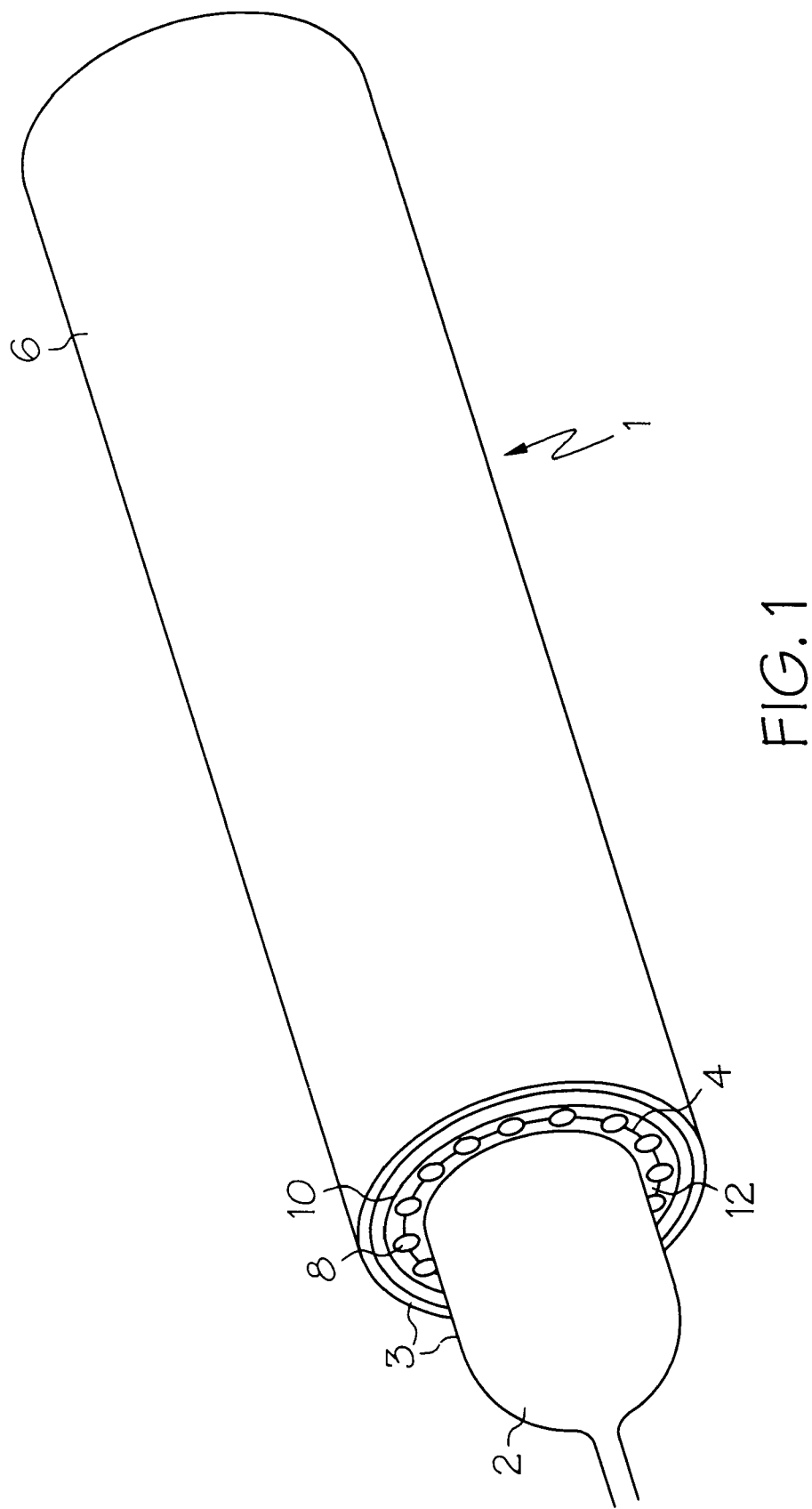
FIG. 1 is a perspective showing an endoluminal prosthesis with catheter delivery sheath comprising a thin tubular structure.
Figure 2:
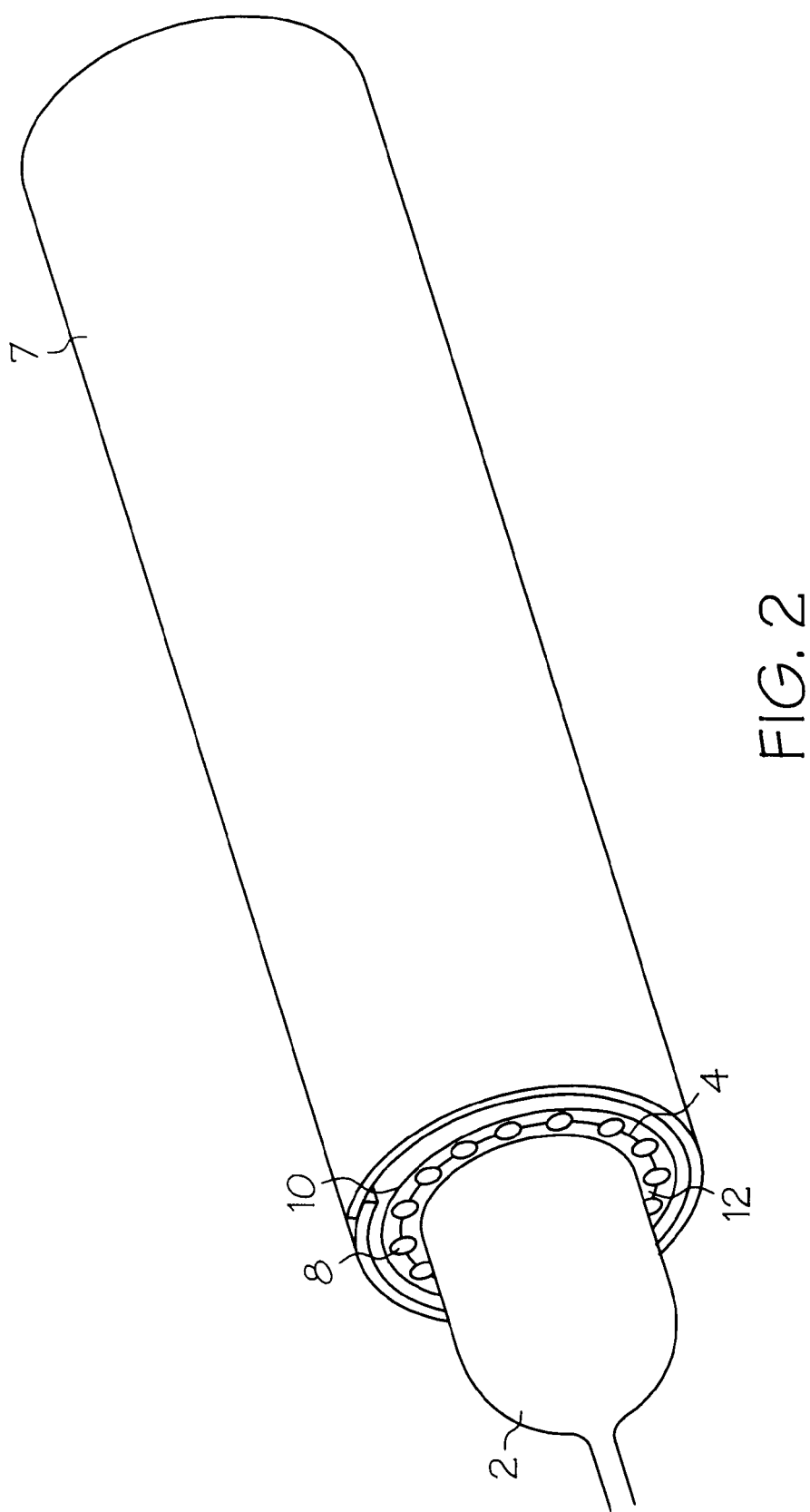
FIG. 2 is a perspective showing an endoluminal prosthesis with catheter delivery sheath comprising a sheet formed into a tube.

Referring now to FIGS. 1 and 2 of the drawings, the delivery system 1 of the present invention includes a delivery catheter 3 having an expandable balloon 2 at one end. As is well known in the catheter art, catheter 3 may be used in delivering a balloon-expandable prosthesis 4. The endoluminal prosthesis 4 shown in FIGS. 1 and 2 is a composite stent/graft device which includes a radially distensible stent 8 with an exterior cover 10, and an interior cover 12. As above described, prosthesis 4 is expandable from a non-expanded or collapsed delivery configuration to an expanded deployed configuration. Prosthesis 4 is radially distensible upon an expansive force. The expansive force may be applied by expansion of balloon 2 or may be derived from self-expansion of the prosthesis itself.

Delivery catheter sheath 6 is an elongate thin walled tube which surrounds the prosthesis 4 and supports the prosthesis over balloon catheter 2. Sheath 6 retains prosthesis 4 in a non-expanded state during catheter delivery. Such retention of the prosthesis is provided by constructing sheath 6 to have a yield strength which is greater than a first expansive force required to expand prosthesis 4 from its collapsed configuration to its expanded configuration. The yield strength of catheter sheath 6 is therefore sufficiently strong to retain prosthesis 4 in a contracted state on balloon 2 during delivery of the prosthesis. The elongate tube forming delivery catheter sheath 6 may be formed from an extruded tube shown in FIG. 1, or from an extruded sheet formed into a tube, as shown in FIG. 2. While the yield strength of catheter sheath 6 is sufficient to retain prosthesis 4 in a non-expanded configuration during delivery of the prosthesis, the yield strength is sufficiently less than a second expansive force which is applied to prosthesis 4 in order to deploy the prosthesis. This second expansive force is typically derived from the expansion of balloon catheter 2. Catheter sheath 6 is therefore formed in order to provide the yield strength which is sufficient to maintain the prosthesis in a collapsed delivery condition, yet is inelastically expanded upon application of a greater force so as to permit deployment of the prosthesis. A variety of sheath constructions are contemplated within the present invention so that the appropriate yield strength may be imparted to the sheath. More particularly, a material is selected with the desirous yield strength properties. Furthermore sheath 6 may also be constructed with tubular walls with a particularly thin cross-section appropriate to impart the desirous yield strength. Still further, weak points in the tube may be deliberately introduced to give pre-determined yield points within sheath 6. Sheath 6 is typically formed of a polymeric material by extrusion and stretching techniques commonly known in the art. Standard extrusion techniques such as those discussed in U.S. Pat. Nos. 3,953,566, 3,962,153 and 4,187,390 may be employed.

In order to effectively deliver prosthesis 4, the following procedure is preferably followed. Prosthesis 4 is loaded within delivery sheath 6 in a reduced delivery diameter. As mentioned above, sheath 6 has a yield strength sufficient to retain prosthesis 4 in this reduced diameter. An unexpanded balloon catheter is then inserted within prosthesis 4. As also noted above, delivery catheter 3 includes an expandable balloon 2 for supporting said prosthesis and is expandable under a radially expansive force. The prosthesis 4, sheath 6, and balloon catheter 2 are delivered intraluminally to the implantation site, however, in a contracted state. Once delivered to the implantation site, a radially expansive force is applied to balloon catheter 2. This radially expansive force is applied by inflating balloon 2 with a fluid as is well known in the catheter art. The applied radially expansive force supplied by balloon expansion is sufficient to surpass the yield strength of sheath 6. This causes the sheath 6 to expand allowing the prosthesis to expand to its expanded position. Sheath 6 therefore allows expansion and implantation of prosthesis 4 with the application of this radially expansive force by its thin tubular walls expanding past their yield strength. The initial inelasticity of sheath 6 during delivery allows successful implantation of prosthesis 4. As more fully described by the following embodiments and drawings, the appropriate yield strength of the delivery sheath may be provided in a number of ways. In FIGS. 1 and 2, the thin walled polymeric material forms the sheath itself and provides the appropriate yield strength.

As used in this specification, the term yield strength refers to the stress level at which the material can no longer elastically resist permanent deformation. After a material has been stretched beyond a certain point, the material remains fixed in its stretched condition. This type of stretching causes the material to either undergo inelastic strain, commonly referred to as plastic deformation, or it may cause the material to fracture. Often, the material undergoes first inelastic strain, then fracture. In any case, delivery sheath 6 is inelastically expanded and is no longer able to radially restrain prosthesis 4.

Once released from radial restraint of the sheath 6 and expanded, the prosthesis remains patent in the lumen. Upon expansion, sheath 6 may remain implanted with prosthesis 4 or it may be removed. If it is desired to remain implanted with the prosthesis, sheath 6 may be constructed of material of sufficiently biocompatible properties so it will not interfere with assimilation of the prosthesis in vivo. Such biological assimilation and incorporation includes endothelialization, and other adaptive measures taken by the body in response to the implant. Polytetrafluoroethylene is an example of a polymeric material with a microporous structure to allow biologic assimilation.

Figure 4:
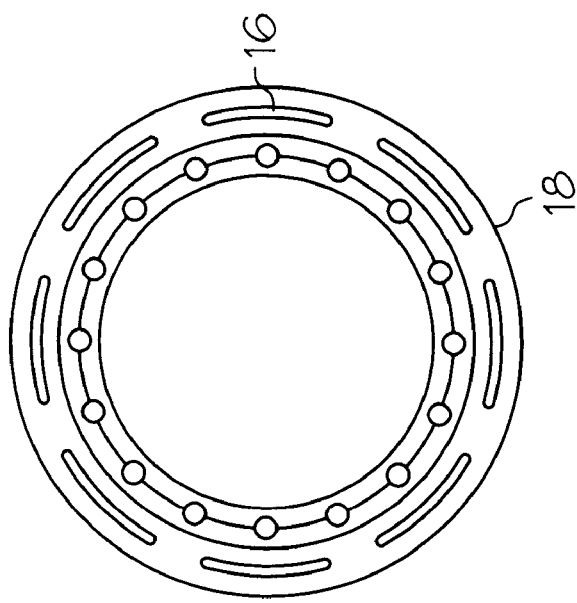
FIG. 4 is a cross-section showing of the prosthesis and catheter sheath of FIG. 3 in a diametrically expanded state.
Figure 3:
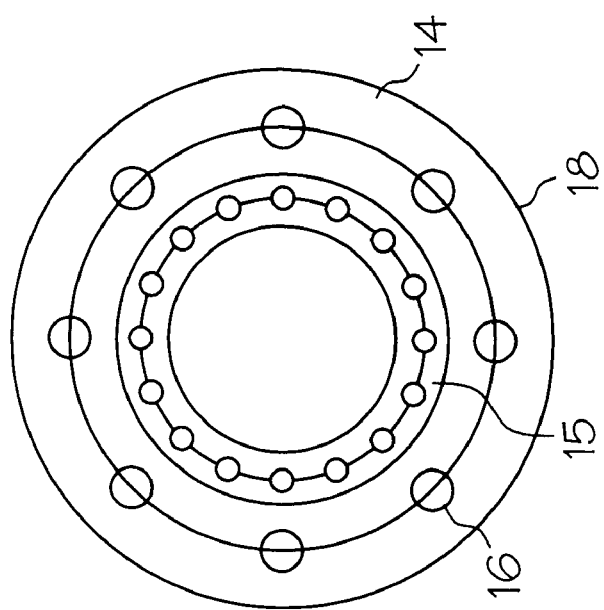
FIG. 3 is a cross-section showing an endoluminal prosthesis with catheter delivery sheath comprising two polymeric materials, one of said materials being in the form of longitudinally extending segments intermittently embedded within the other material.

Referring now to FIGS. 3 and 4 of the drawings, a further embodiment of the delivery system of the present invention is shown. The delivery sheath 14 is a tubular body formed of two different polymeric materials. Sheath 14 includes a plurality of longitudinally extending segments 16 formed of a first polymeric material intermittently embedded within tubular body 18 of a second polymeric material. The first and second polymeric materials of the sheath as well as their shape and construction may be varied according to the desired properties of yield strength in relation to each other.

Figure 4A:
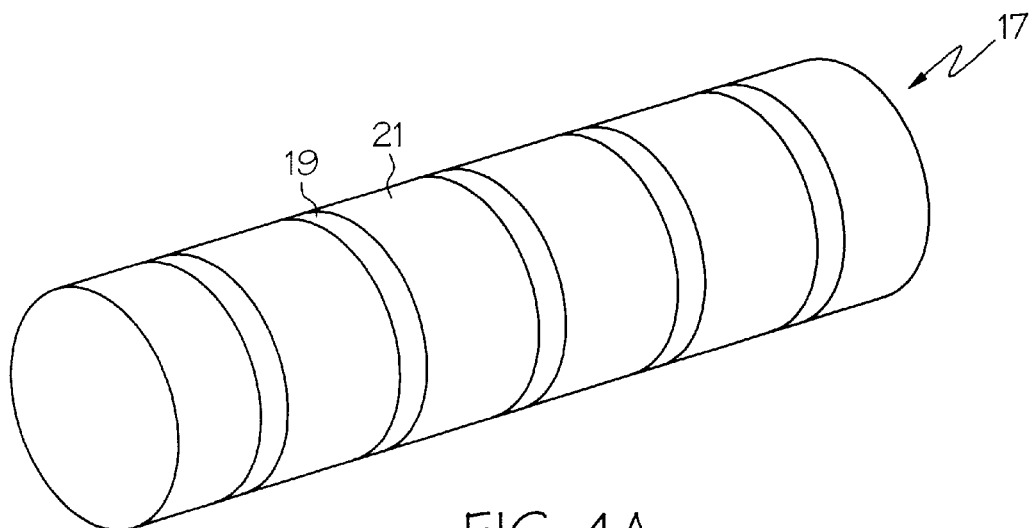
FIG. 4A is a perspective showing of a catheter sheath of the present invention with circumferential segments intermittently embedded within a polymeric material.

Referring now to FIG. 4A of the drawings, delivery sheath 17 can be a tube having a circumference and a longitudinal axis, and comprising a first polymeric material and a second polymeric material. Said first polymeric material comprises circumferential segments 19 intermittently embedded within said second polymeric material 21 (which is formed into a tubular body) and disposed transverse to said longitudinal axis. Circumferential segments 19 may be a continuous helix wrapped circumferentially around said sheath, or segments 19 may be intermittently independent ring segments, each forming a continuous loop circumferentially around said sheath 17.

In one embodiment, first polymeric material 16 (or 19) has a yield or tensile strength greater than that of second polymeric material 18 (or 21). In this embodiment a radially expansive force applied to the sheath will cause the sheath to stretch at the preselected areas occupied by the second polymeric material 18 (or 21). Accordingly, first polymeric material 16 (or 19) will provide strength to the sheath, and prevent axial expansion of the graft.

In another embodiment, first polymeric material 16 (19) possesses a tensile strength less than that of polymeric material 18 (21). In this embodiment, a radially expansive force applied to the sheath will cause the sheath to stretch at segmented areas of polymeric material 16 (19). Second polymeric material 18 (21), in which first polymeric material 16 (19) is embedded will provide structural integrity and strength while the sheath stretches in the preselected areas of longitudinal segments. FIG. 3 shows the prosthesis and catheter sheath of FIG. 2 in a radially expanded position. The first polymeric material 16, because it is of lesser tensile strength, provides the yielding area for the sheath. The first and second polymeric material may be formed of a variety of material. Furthermore, various grades and durometers of the same base resin or composite assemblies of different base resins, as well as any number of combinations or alloys of materials may be used as either material in the sheath. Some materials which may be used in the sheath include, but are not limited to nylon (polyamide), polyurethane (PU), polyimide (PI), polytetrafluoroethylene (PTFE), expanded polytetrafluoroetylene (ePTFE), polyether ether ketone (PEEK), fluorinated ethylene propylene (FEP), and polybutylene terephthalate (PBT), as well as other thermoplastic elastomers not mentioned.

The combination of materials comprising delivery sheath 14 in FIGS. 3, 4 and 4A, and their corresponding tensile strengths, therefore, provides catheter sheath 14 and 17 with a yield strength greater than a first radially expansive force of prosthesis 15. Similar to the sheath described above in FIGS. 1 and 2, the yield strength of sheath 14 and 17 is less than that of a second radially expansive force which is either applied by a self-expansion mechanism of the prosthesis, or by the expansion of the balloon to said catheter. Similarly, application of the second expansive force deploys the prosthesis within the lumen. After deployment, catheter sheath 14 may remain implanted within the lumen, or may subsequently be withdrawn. A preferred method of making catheter sheath 14 is by co-extrusion of the two polymeric materials together by the above mentioned extrusion techniques.

Figure 5:
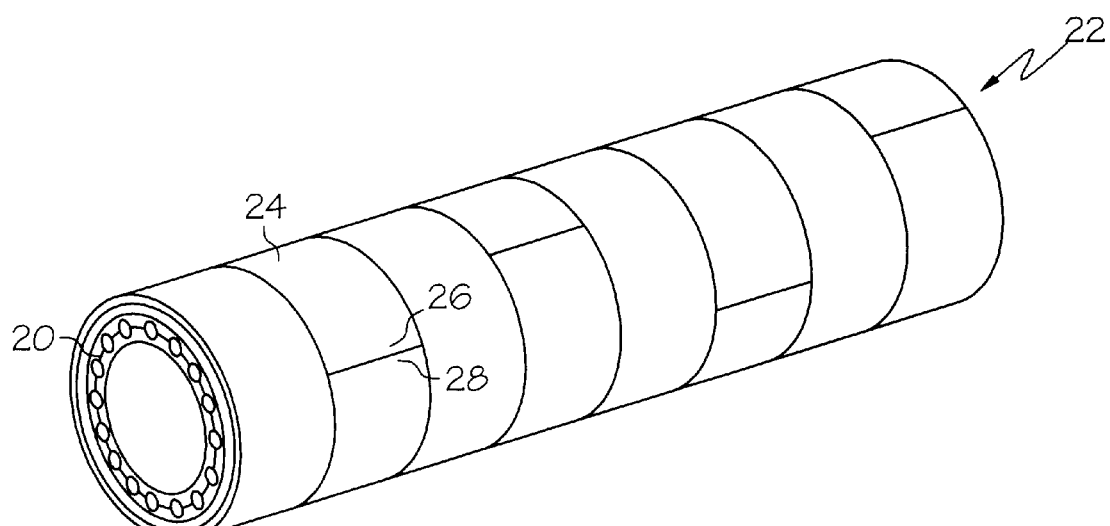
FIG. 5 is a perspective showing an endoluminal prosthesis with a catheter delivery sheath comprised of polymeric strips circumferentially wrapped around said prosthesis transversely to a longitudinal axis of said prosthesis.
Figure 6:
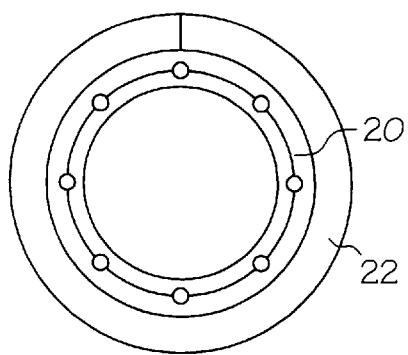
FIG. 6 is a cross-section showing the prosthesis and catheter sheath of FIG. 5 in a diametrically expanded state.

Referring now to FIGS. 5 and 6 of the drawings, another embodiment of the present invention is shown. A delivery system comprising an endoluminal prosthesis 20, and a catheter delivery sheath 22 is shown. Delivery sheath 22 of FIG. 4 is comprised of polymeric strips circumferentially wrapped around said prosthesis transversely to a longitudinal axis of said prosthesis. Polymeric strips 24 possess a first end 26 and a second end 28. First end 26 and second end 28 may abut or overlap to form a circumferential loop around a longitudinal axis of the prosthesis and meet at a selected area of the sheath. First end 26 and second end 28 may be adhered together at their meeting point, may be adhesively adhered together at their meeting point, may be adhered to the prosthesis at their meeting point, or may be adhesively adhered to the prosthesis at the meeting point.

The term adhered as used herein is used to refer to any means of securing components together without the use of an adhesive. Some examples include, thermal bonding, sintering, or, fastening through other mechanical means. Adhesives which may be used vary depend on what type of polymeric material is used as the polymeric strip. The polymeric strip may be formed of polytetrafluoroethylene (PTFE), ePTFE, polyurethane, fluorinated ethylene propylene (FEP), polyether ether ketone, polyimide, nylon (polyamide), polybutylene terephthalate as well as other thermoplastic elastomers. Some adhesives which may be used include FEP, polyurethane adhesives, silicones, cryanoacrylates, and epoxies.

Similar to the delivery system shown in FIGS. 1–4, the delivery system shown in FIGS. 5 and 6 comprises a prosthesis 20, said prosthesis being radially expandable under a first radially expansive force and a second radially expansive force. A balloon catheter 2 as shown in FIG. 1 may be expanded to supply said second radially expansive force, said second radially expansive force being greater than said first expansive force of said prosthesis. Catheter sheath 22 of FIGS. 5 and 6 possesses a yield strength which is greater than the first expansive force of said prosthesis, and less than said second expansive force of the balloon catheter. Upon application of the second expansive force, delivery sheath 22 of FIG. 5 allows implantation of the prosthesis, as the yield strength of delivery sheath 22 is less than the second expansive force. The application of the second expansive force therefore effectively deploys the prosthesis, as it surpasses the yield strength of the sheath, and the prosthesis is expanded to its active radius. The yield strength of sheath 22 is provided by its configuration, particularly the area where ends 26 and 28 of the polymeric strips meet. The seam where the strips meet each other may provide an area of decreased strength, depending on how the ends are adhered to each other, or to the prosthesis. These weak points provide "break-away" points which allow deployment of the prosthesis without movement of the exterior sheath.

Figure 14:
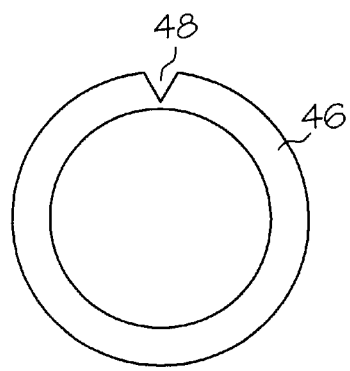
FIG. 14 is a cross-section showing a sheath with a longitudinally extending notch.
Figure 15:
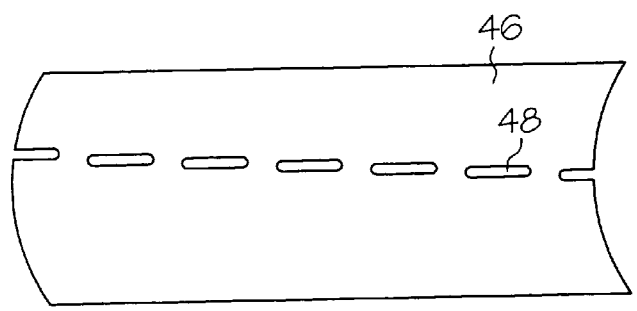
FIG. 15 is a perspective showing a plurality of longitudinally extending slits in a delivery sheath.

In addition to "break-away" points, an area of decreased tensile strength can be constructed into a delivery sheath in a number of ways. For example, notches can be engineered into any of the sheaths disclosed in the present invention. The term notches, as used herein, means an area of decreased tensile strength in a sheath. Notches are typically longitudinally extending slits in the delivery sheath. In a preferred embodiment a delivery sheath includes a plurality of longitudinally aligned slits. A notch can be engineered into a sheath in a number of different ways, including simply cutting away a section of a sheath. Notches can be further lined up along a longitudinal axis of a delivery sheath to provide a line of decreased resistance in the delivery sheath. Such a line provides a line in the sheath for a controlled expansion of the sheath similar to a line of perforation. A notch can be anywhere from 1 to 400 millimeters long, preferably in the range of 5 to 10 millimeters. Notches can be on either a luminal or exterior surface of a tubular sheath. The aligned notches can be in the range of 1 to 400 millimeters long. Referring now to FIGS. 14 and 15 of the drawings, a delivery sheath 46 is shown with slits 48 longitudinally extending throughout the delivery sheath.

FIG. 6 shows a cross-section of such a delivery system after an expansive deformation has taken place. The polymeric strips comprising delivery sheath may be formed of PTFE, ePTFE, FEP, PEEK, PI, nylon, polyurethane, PE, PBT, and other thermoplastic elastomers, not mentioned.

Figure 7:
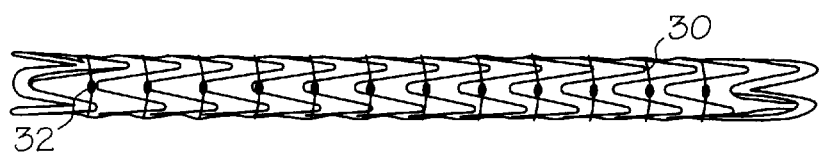
FIG. 7 is a perspective showing an endoluminal prosthesis with a catheter delivery sheath comprising loops of yarn oriented transversely to a longitudinal axis of the prosthesis.
Figure 8:
FIG. 8 is a perspective showing the prosthesis and catheter sheath of FIG. 7 in an expanded state.

Referring now to FIGS. 7 and 8 of the drawings, another embodiment of the present invention is shown. FIG. 7 shows a perspective of the delivery system of the present invention wherein the delivery sheath is comprised of polymeric strips 30, and said polymeric strips are comprised of a thin suture. Polymeric strips comprising the delivery sheath may be formed of such a suture, but also may be formed of a yarn, ribbon, or thread. Polymeric strips 30 may have a predetermined section of decreased tensile strength 32, which upon expansion of the prosthesis, yields to allow implantation of the prosthesis. FIG. 8 is a perspective showing an expanded prosthesis with polymeric strips allowing implantation in such a manner.

Figure 9:
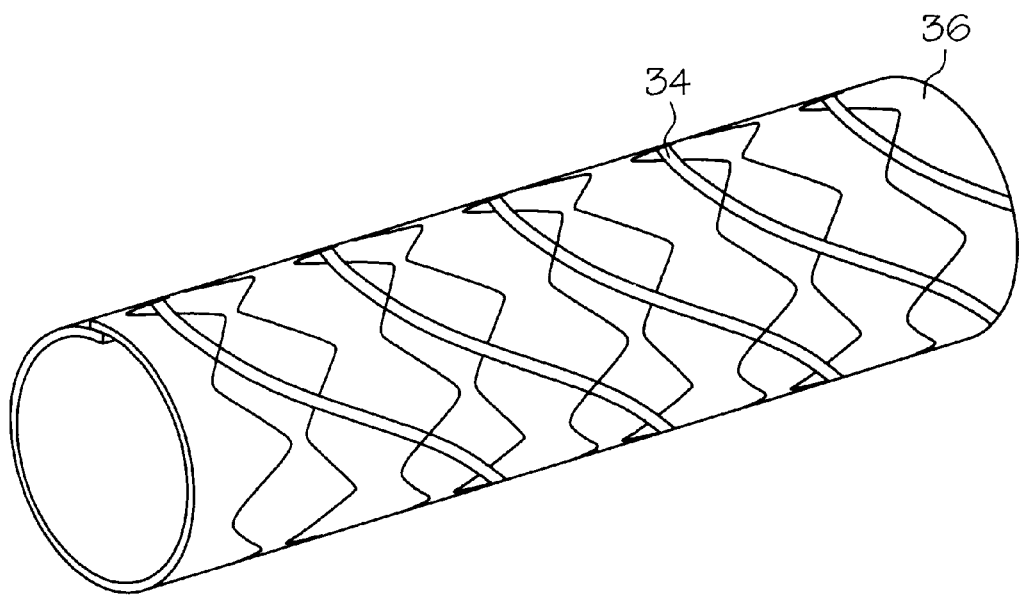
FIG. 9 is a perspective showing an endoluminal prosthesis with a catheter delivery sheath comprising a continuous helical wrap of a polymeric material.
Figure 10:
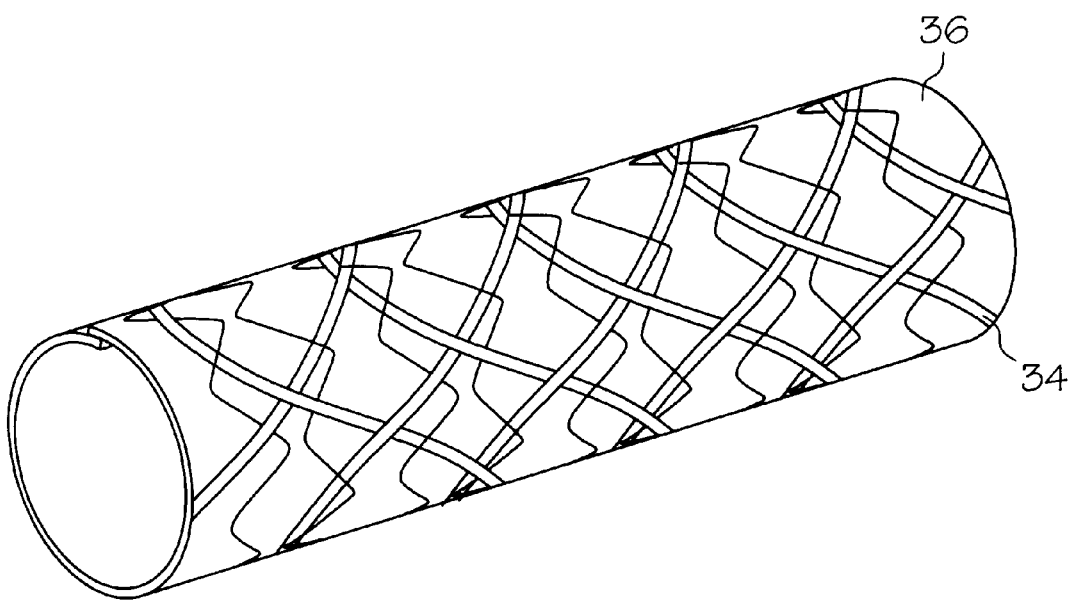
FIG. 10 is a perspective showing an endoluminal prosthesis with a catheter delivery sheath comprising a multi-directional helical wrap of a polymeric material.

Referring now to FIGS. 9 and 10 of the drawings, another embodiment of the present invention is shown. FIG. 9 shows a perspective of the delivery system of the present invention wherein the delivery sheath is comprised of polymeric strips 34 wound helically in a continuous band around, through, or within stent/graft prosthesis 36. The continuous winding is shown with a tape-like polymeric winding, but other forms are contemplated within the present invention. The continuous helical winding may be with a thin suture, yarn, ribbon, or thread. The predetermined yield strength of the delivery sheath may be achieved as a result of the material used, the thinness of the material, or with a predetermined section of decreased tensile strength which may be manufactured into the sheath.

Figure 11:
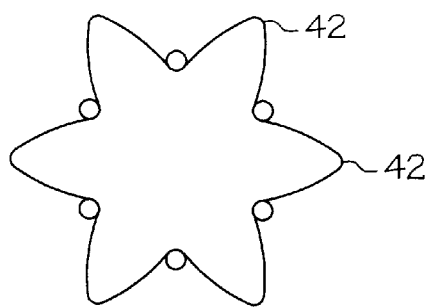
FIG. 11 is a cross-section showing another embodiment of the present invention, a stent with a tubular covering.
Figure 12:
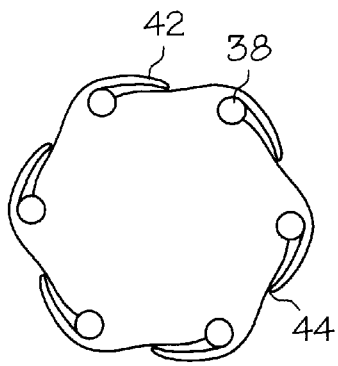
FIG. 12 is a cross-section showing a stent with tubular covering in a collapsed condition of reduced diameter.
Figure 13:
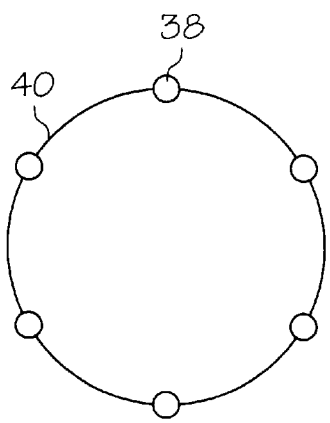
FIG. 13 is a cross-section showing a stent with a tubular covering in collapsed condition, the tubular cover adhered to itself at selected areas.

Referring now to FIGS. 11–13 of the drawings, yet another embodiment of the present invention is shown. A prosthesis, stent 38 is shown in cross-section in FIG. 11 in its expanded state a with a tubular cover 40. Tubular cover 40 is integrally associated with stent 38. Tubular structure 40 is placed circumferentially on the exterior surface of stent 38 in its expanded state, where it is held taught by the expanded stent. Tubular cover 40 may also be placed circumferentially on the interior of stent 38, or on both sides. The stent may be on a mandrel. The stent is then collapsed, and reduced in diameter to its compressed condition as shown in FIG. 12. This leaves areas of slack 42 in tubular cover 40 as seen in the cross-section in FIG. 12. The selected portions of slack 42 of tubular cover 38 are then wrapped around stent 38 folded over itself as seen in the cross-section shown in FIG. 13. Tubular cover 40 is then adhered to itself at selected areas 44 of the cover. The adhesion may take place by any means discussed above, including adhesively adhering, sintering, thermal adhesion, or adhesion by other mechanical means. The tubular cover may be comprised of a number of polymeric materials, including but not limited to a polymer selected from the group consisting of PTFE, ePTFE, nylon, polyurethane, polyimide, polyether ether ketone, fluorinated ethylene propylene, and polybutylene terephthalate.

This embodiment is particularly useful because the tubular cover is integrally associated with the prosthesis, and a reduced profile is created for the delivery system, which provides for easier, and more efficient delivery of the prosthesis. The selected areas of adhesion 44 provide for an area of decreased tensile strength with respect to the tubular cover. In a preferred embodiment, a balloon catheter is inserted within the stent 38, and expansion of the balloon catheter ruptures the tubular cover 40 at areas of adhesion 44. In a preferred embodiment, tubular cover 40 is biocompatible or biodegradable and may be assimilated within the body, and remains implanted with stent 38.

Another advantage of the present invention is that in certain embodiments, it is possible to allow the delivery sheath to remain implanted with the prosthesis after implantation. Additionally, a sheath may be comprised of bioabsorbable materials. The term bio-absorbable as used in this disclosure is synonymous with biodegradable, meaning the ability to be degraded by processes involving biological conditions, such as those present in the bodies of humans or other animals. More specifically, this term indicates the physical or chemical breaking down of the polymer into smaller units which are preferably innocuous, non-toxic and are readily eliminated or metabolized by the body. Some bio-absorbable materials which may be used include polymers, copolymers, block polymers, and mixtures thereof Bio-absorbable polymers and polymer classes include, but are not limited to the following: poly(glycolic acid) (PGA), poly(lactic acid) (PLA), polydioxanes, polyoxalates, poly(α-esters), polyanhydrides, polyacetates, polycaprolactones, poly(orthoesters), polyamino acids, polyurethanes, polycarbonates, polyiminocarbonates, polyamides, poly(alkyl cyanoacrylates), and mixtures and copolymers thereof. Additional useful polymers include, stereopolymers of L- and D-lactic acid, copolymers of bis(p-carboxyphenoxy) proprionic acid and sebacic acid, sebacic acid copolymers, copolymers of caprolactone, poly (lactic acid)/poly(glycoclic acid)/polyethyleneglycol copolymers, copolymers of polyurethane and poly(lactic acid), copolymers of α-amino acids, copolymers of α-amino acids and caproic acid, copolymers of α-benzyl glutamate and polyethylene glycol, copolymers of succinate and poly (glycols), polyphosphazene, polyhydroxy-alkanoates and mixtures thereof. Binary and ternary systems are contemplated.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention, and it is intended to claim all such changes and modifications to fall within the scope of the invention.

What is claimed is:

1. An endoluminal prosthesis delivery system comprising:
    a tubular endoluminal prosthesis having a luminal surface and an opposed exterior in surface, said prosthesis being radially expandable from a compressed position under a first radially expansive force and a second radially expansive force greater than said first expansive force; and
    a delivery sheath maintaining said prosthesis in said compressed condition, said delivery sheath possessing a yield strength greater than said first expansive force of said prosthesis, and less than said second expansive force, wherein the delivery sheath is a tube having a longitudinal axis and comprising a first polymeric material and a second polymeric material, said first polymeric material comprising longitudinally extending segments intermittently embedded within said second polymeric material and extending parallel to said longitudinal axis.

2. The delivery system according to claim 1 further comprising a balloon catheter having an expandable balloon for supporting said prosthesis, said balloon applying said second radially expansive force to said prosthesis.

3. The delivery system according to claim 1 wherein said prosthesis is self-expanding.

4. The delivery system according to claim 1 wherein said delivery sheath is a thin wall tube comprised of polymeric material.

5. The delivery system according to claim 4 wherein said tube is an extruded tube.

6. The delivery system according to claim 4 wherein said tube is a sheet formed into a tube.

7. The delivery system according to claim 4 wherein said polymeric material is selected from the group consisting of nylon, polyurethane, polytetrafluoroethylene(PTFE), ePTFE, fluorinated ethylene propylene, polyimide, polyether ether ketone, and polybutylene terephthalate.

8. The delivery system according to claim 1 wherein said first polymeric material possesses a first tensile strength and said second polymeric material possesses a second tensile strength greater than said first tensile strength.

9. The delivery system according to claim 1 wherein said first polymeric material possesses a first tensile strength and said second polymeric material possesses a second tensile strength less than said first tensile strength.

10. The delivery system according to claim 1 wherein said prosthesis may be implanted within a human body.

11. The delivery system according to claim 10 wherein said delivery sheath may remain with said prosthesis after implantation within a human body.

12. The delivery system of claim 1 wherein said delivery sheath is bio-absorbable.

13. The delivery system according to claim 1 wherein said endoluminal prosthesis comprises a stent.

14. The delivery system according to claim 13 wherein said delivery sheath is a tubular cover integrally associated with said prosthesis, said tubular cover adhered to itself at selected areas of decreased tensile strength.

* * * * *